United States Patent
Yamashita et al.

(10) Patent No.: US 10,222,385 B2
(45) Date of Patent: *Mar. 5, 2019

(54) METHODS FOR DISCRIMINATING BETWEEN PROSTATE CANCER AND A BENIGN PROSTATE-DISEASE

(71) Applicant: KONICA MINOLTA, INC., Chiyoda-ku, Tokyo (JP)

(72) Inventors: Katsuko Yamashita, Yokohama (JP); Takatoshi Kaya, Inagi (JP); Youichi Ide, Wako (JP); Tomonori Kaneko, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/108,286

(22) PCT Filed: Dec. 27, 2013

(86) PCT No.: PCT/JP2013/085116
§ 371 (c)(1),
(2) Date: Jun. 24, 2016

(87) PCT Pub. No.: WO2015/097863
PCT Pub. Date: Jul. 2, 2015

(65) Prior Publication Data
US 2016/0305960 A1    Oct. 20, 2016

(51) Int. Cl.
*G01N 33/68* (2006.01)
*G01N 33/574* (2006.01)
*G01N 33/573* (2006.01)

(52) U.S. Cl.
CPC ....... *G01N 33/6893* (2013.01); *G01N 33/573* (2013.01); *G01N 33/57434* (2013.01); *G01N 2333/4725* (2013.01); *G01N 2333/705* (2013.01); *G01N 2333/96455* (2013.01); *G01N 2800/342* (2013.01)

(58) Field of Classification Search
None
See application file for complete search history.

(56) References Cited

U.S. PATENT DOCUMENTS

| | | | |
|---|---|---|---|
| 5,591,589 A | 1/1997 | Katoh et al. | |
| 5,866,433 A | 2/1999 | Schalkhammer et al. | |
| 8,039,609 B2 | 10/2011 | Missailidis et al. | |
| 8,883,977 B2 | 11/2014 | Nishimura et al. | |
| 2004/0147033 A1 | 7/2004 | Shriver et al. | |
| 2005/0042209 A1* | 2/2005 | Kufe | C07K 14/4727 424/93.21 |
| 2005/0180997 A1 | 8/2005 | Benita et al. | |
| 2008/0074671 A1 | 3/2008 | Ohtsuka et al. | |
| 2008/0293147 A1 | 11/2008 | Machida et al. | |
| 2009/0061455 A1 | 3/2009 | Sankaran et al. | |
| 2009/0286854 A1 | 11/2009 | Missailidis et al. | |
| 2010/0087363 A1 | 4/2010 | Rubinstein et al. | |
| 2010/0216163 A1 | 8/2010 | Kuballa et al. | |
| 2010/0272707 A1 | 10/2010 | Bay et al. | |
| 2011/0129849 A1 | 6/2011 | Zhang et al. | |
| 2011/0294141 A1 | 12/2011 | Yamashita et al. | |
| 2012/0065089 A1 | 3/2012 | Kuno et al. | |
| 2012/0282612 A1 | 11/2012 | Yamashita et al. | |
| 2013/0045543 A1 | 2/2013 | Nishimura et al. | |
| 2013/0116142 A1 | 5/2013 | Watson et al. | |
| 2013/0123137 A1 | 5/2013 | Reichardt et al. | |
| 2014/0162888 A1 | 6/2014 | Kuslich et al. | |
| 2014/0170772 A1 | 6/2014 | Ide et al. | |
| 2014/0186853 A1 | 7/2014 | Yamashita et al. | |
| 2015/0140571 A1 | 5/2015 | Kaneko et al. | |
| 2016/0138118 A1 | 5/2016 | Yamashita et al. | |
| 2016/0305960 A1 | 10/2016 | Yamashita et al. | |
| 2016/0313337 A1 | 10/2016 | Yamashita et al. | |

FOREIGN PATENT DOCUMENTS

| | | |
|---|---|---|
| EP | 653640 A1 | 5/1995 |
| EP | 2395357 A1 | 12/2011 |
| JP | 61292062 A | 12/1986 |
| JP | 04130274 A | 5/1992 |
| JP | 07191027 A | 7/1995 |
| JP | 3562912 B2 | 9/2004 |
| JP | 2008102117 A | 5/2008 |
| JP | 2008529967 A | 8/2008 |
| JP | 2009053195 A | 3/2009 |
| JP | 2009535051 A | 10/2009 |
| JP | 2010060293 A | 3/2010 |
| JP | 2010127827 A | 6/2010 |
| JP | 2010145272 A | 7/2010 |

(Continued)

OTHER PUBLICATIONS

Ohyabu et al. (J. Am. Chem. Soc., 131: 17102-17109, 2009).*

(Continued)

*Primary Examiner* — Nelson B Moseley, II
(74) *Attorney, Agent, or Firm* — Holtz, Holtz & Volek PC

(57) ABSTRACT

A method of analyzing diagnostic information, the method including: measuring the concentration of all mucin-1s (total MUC1) in a blood sample originated from a subject to be diagnosed; comparing the measured value with a threshold value; and estimating that a disease affecting the subject to be diagnosed is not prostate cancer but a benign prostate disease when the measured value of the concentration of total MUC1 is greater than the threshold value.

13 Claims, 2 Drawing Sheets

(56) References Cited

FOREIGN PATENT DOCUMENTS

| JP | 2011080935 A | 4/2011 | | |
|---|---|---|---|---|
| JP | 2011137754 A | 7/2011 | | |
| JP | 2012255736 A | 12/2012 | | |
| JP | 2013076666 A | 4/2013 | | |
| JP | 2013526852 A | 6/2013 | | |
| JP | 5231247 B2 | 7/2013 | | |
| WO | 2005064333 A1 | 7/2005 | | |
| WO | 2007129114 A2 | 11/2007 | | |
| WO | 2010090264 A1 | 8/2010 | | |
| WO | WO/2010/090264 | * | 8/2010 | ........... G01N 33/574 |
| WO | 2010100862 A1 | 9/2010 | | |
| WO | 2010123073 A1 | 10/2010 | | |
| WO | 2010134592 A1 | 11/2010 | | |
| WO | 2011052244 A1 | 5/2011 | | |
| WO | 2011135869 A1 | 11/2011 | | |
| WO | 2011161150 A1 | 12/2011 | | |
| WO | 2012173228 A1 | 12/2012 | | |
| WO | 2013054281 A1 | 4/2013 | | |
| WO | 2013070089 A1 | 5/2013 | | |

OTHER PUBLICATIONS

K. Yamashita, et al., "Carbohydrate Structures of Nonspecific Cross-reacting Antigen-2, a Glycoprotein Purified from Meconium as an Antigen Cross-reacting with Anticarcinoembryonic Antigen Antibody", Journal of Biol. Chem., vol. 264, 30, Oct. 25, 1989.
K. Yamashita, et al., "Structural Studies of the Carbohydrate Moieties of Carcinoembryonic Antigens", Cancer Research, 47, Jul. 1, 1987, pp. 3451-3459 (in English).
K. Yamashita, et al., "Sugar Chains of Human Cord Serum a-Fetoprotein: Characteristics of N-linked Sugar Chains of Glycoproteins Produced in Human Liver and Hepatocellular Carcinomas", Cancer Research, 53, Jul. 1, 1993, pp. 2970-2975 (in English).
Burke, et al., "Characterization of MUC1 glycoprotein on prostate cancer for selection of targeting molecules", International Journal of Oncology, vol. 29, Issue 1, Jul. 2006, pp. 49-545.
Devine, et al., "Prostate-specific antigen (PSA) and cancer-associated serum antigen (CASA) in distinguishing benign and malignant prostate diesase", International Journal of Biological Markers, vol. 10, No. 4, Jan. 1995, pp. 221-225.
Fukushima, et al., "α1,2-Fucosylated and β-N-acetylgalactosaminylated prostate-specific antigen as an efficient marker of prostatic cancer", Glycobiology, vol. 20, No. 4, pp. 452-460, Apr. 1, 2010.
Matsuda, et al., "Wisteria floribunda Agglutinin-Positive Mucin 1 is a Sensitive Biliary Marker for Human Cholangiocarcinoma", Hepatology, 2010, vol. 52, No. 1, pp. 174-182.
Mislovicova, et al., "Lectinomics L Relevance of exogenous plant lectins in biomedical diagnostics", Biologia, vol. 64, No. 1, 2009, pp. 1-19.
Narimatsu, et al., "A strategy for discovery of cancer glycobiomarkers in serum using newly developed technologies for glycoproteomics", The FEBS Journal; Jan. 2010, pp. 95-105, vol. 277, No. 1.
Takeya, et al., "Presence of β-linked GalNAc residues on N-glycans of human thyroglobulin", Life Sciences, Pergamon Press, vol. 80, No. 6, pp. 538-545, Jan. 6, 2007.
U.S. Appl. No. 15/108,283; First Named Inventor: Katsuko Yamashita; Title: "Method for Analyzing Information for Diagnosis and Kit Therefor"; filed Jun. 24, 2016.
U.S. Appl. No. 14/396,646; First Named Inventor: Tomonori Kaneko; Title: "Antigen Detection Method Which Uses Lectin and Comprises Enzyme Treatement Step"; filed Oct. 23, 2014.
Devine, et al., Serum Mucin Antigens CASA and MSA in Tumors of the Breast, Ovary, Lung, Pancreas, Bladder, Colon, and Prostate, Cancer, vol. 72, No. 6, Sep. 15, 2003, pp. 2007-2015.
Falsaperla, et al., "Role of Ca 15-3 in patients with biochemically suspected prostate cancer and multiple negative ultrasound-guided prostate biopsies", Prostate Cancer and Prostatic Diseases, vol. 6, No. 1, Jan. 1, 2003, pp. 45-49.
Ohyabu, et al., "An Essential Epitope of Anti-MUC1 Monoclonal Antibody KL-6 Revealed by Focused Glycopeptide Library", Journal of the American Chemical Society, vol. 131, No. 47, Dec. 2, 2009, pp. 17102-17109.
Rubinstein, et al., Application of Immunohistologic Staining to Develop a Malignant Index to Aid in Distinguishing Benign From Malignant Prostatic Tissue, The Prostate, vol. 14, No. 1, Wiley-Liss, New York, NY, Jan. 1, 1989, pp. 383-388.
Extended European Search Report (EESR) dated Jul. 7, 2017 issued in counterpart European Application No. 13900337.0.
Office Action (Non-Final Rejection) dated Jun. 30, 2017 issued in U.S. Appl. No. 15/108,283.
Japanese Office Action (and English translation thereof) dated Sep. 12, 2017 issued in Japanese Application No. 2015-554445.
Office Action (Non-Final Rejection) dated Sep. 18, 2017 issued in related U.S. Appl. No. 14/396,646.
International Search Report (ISR) including Written Opinion dated Mar. 4, 2014, issued in counterpart International Application No. PCT/JP2013/085116.
Devine, et al., "Prostate-specific antigen (PSA) and cancer-associated serum antigen (CASA) in distinguishing benign and malignant prostate disease", The International Journal of Biological Markers, 1995, vol. 10, No. 4, pp. 221-225.
Xiang, et al., "Tumor infiltrating dendritic cells and Mucin1 gene expression in benign prostatic hyperplasia and prostate cancer", National Journal of Andrology, 2003, vol. 9, No. 7, pp. 497-500, Abstract.
Japanese Office Action (and an English translation thereof) dated Sep. 5, 2017 issued in Japanese Application No. 2015-554444.
"Lens culinaris lectin (LCA/LcH)", Medicago, <http://www.medicago.se/lens-culinaris-lectin-lcalch>, 2018.
Office Action (Non-Final Rejection) dated Mar. 26, 2018 issued in U.S. Appl. No. 14/396,646.
"Unconjugated Aleuria Aurantia Lectin (AAL)", Vector, <https://vectorlabs.com/unconjugated-aleuria-aurantia-lectin-aal.html>, 2018.
"WGA Lectin (Biotin)", GeneTex, <http://www.genetex.com/WGA-Lectin-Biotin-GTX01501.html> 2018.
Weatherman, et al., "Specificity of C-glycoside complexation by mannose/glucose specific lectins", Biochemistry, vol. 35, No. 11, pp. 3619-3624, Mar. 19, 2016 (Abstract Only).
European Office Action dated Jun. 28, 2018 issued in European Application No. 13900340.4.
European Office Action dated Jun. 21, 2016, issued in European Application No. 13780782.2.
European Office Action dated Nov. 18, 2016, issued in European Application No. 13780782.2.
European Office Action dated Sep. 3, 2018 issued in counterpart European Application No. 13900337.0.
Extended European Search Report (EESR) dated May 10, 2017 issued in European Application No. 13900340.4.
Extended European Search Report dated Aug. 28, 2015, issued in European Application No. 13780782.2.
International Preliminary Report on Patentability (IPRP) including Written Opinion dated Oct. 28, 2014, issued in International Application No. PCT/JP2013/061203.
International Search Report (ISR) dated Jul. 9, 2013 issued in International Application No. PCT/JP2013/061203.
International Search Report (ISR) including Written Opinion dated Mar. 18, 2014, issued in International Application No. PCT/JP2013/085115.
Office Action (Final Rejection) dated Nov. 15, 2016 issued in U.S. Appl. No. 14/396,646.
Office Action (Final Rejection) dated Oct. 2, 2018 issued U.S. Appl. No. 14/396,646.
Office Action (Final Rejection) dated Sep. 29, 2015 issued in U.S. Appl. No. 14/396,646.
Office Action (Non-Final Rejection) dated May 19, 2015 issued in U.S. Appl. No. 14/396,646.
Office Action (Non-Final Rejection) dated May 25, 2016 issued in U.S. Appl. No. 14/396,646.
Ambrosi, et al., "Lectins: tools for the molecular understanding of the glycocode", Org. Biomol. Chem. 2005, 3, 1593-1608, Apr. 11, 2005.

(56) References Cited

OTHER PUBLICATIONS

Pohleven, et al., "Affinity Chromatography of Lecitns", Affinity Chromatography, 46-74, Mar. 21, 2012, retrieved from http://cdn.intechopen.com/pdfs-wm/33048.pdf.
Rabiau, et al., "Immunohistochemical Staining of Mucin 1 in Prostate Tissues", In Vivo 23(2); 203-207, Mar.-Apr. 2009.
Office Action (reissued Final Rejection) dated May 23, 2018 issued in U.S. Appl. No. 15/108,283.
Office Action (Restriction Requirement) dated Mar. 16, 2017 issued in U.S. Appl. No. 15/108,283.
Office Action (withdrawn Final Rejection) dated Apr. 20, 2018 issued in U.S. Appl. No. 15/108,283.
Office Action (Advisory Action) dated Aug. 15, 2018 issued in U.S. Appl. No. 15/108,283.

* cited by examiner

[Fig. 1]
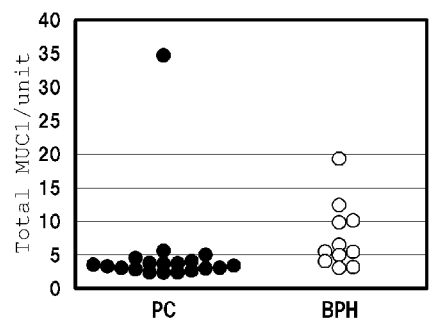
[Fig. 2]
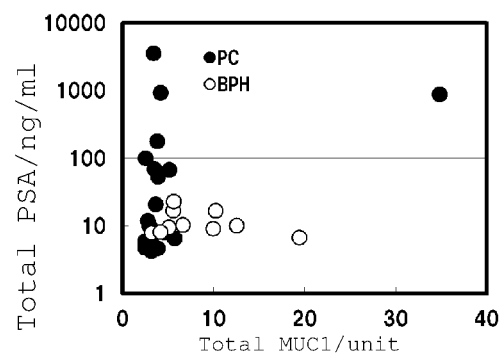

[Fig. 3]
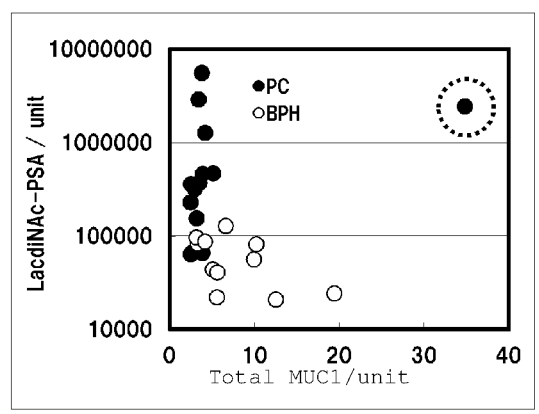

METHODS FOR DISCRIMINATING BETWEEN PROSTATE CANCER AND A BENIGN PROSTATE-DISEASE

TECHNICAL FIELD

The present invention relates to a method of analyzing diagnostic information pertaining to a benign prostate disease and prostate cancer. The present invention also relates to a method of analyzing diagnostic information based on the blood concentration of mucin-1.

BACKGROUND ART

In order to allow proteins bearing a principal role in the biological life functions to orderly and properly exhibit their functions in vivo, post-translation modifications including glycosylation play an extremely important role. With regard to the post-translation modifications, the following findings were gradually made in recent years. The majority of the proteins in a living body are modified with sugar chains, and those sugar chains attached to the proteins play important roles in various aspects of biological phenomena, including protein stability, binding with hormones, binding with toxins, viral infection, mycoplasma infection, bacterial infection, protozoan infestation, fertilization, development and differentiation, cancer cell metastasis, apoptosis and the like. Even when proteins have the same amino acid sequence and the same name, such proteins are modified with a wide variety of sugar chains and, depending on the condition of the protein-producing cells, the structures of the sugar chains are variable and the proteins thus have different roles in vivo.

The relationships between such changes in sugar chains and diseases have also been gradually elucidated. For example, Patent Document 1 describes as follows with regard to prostate-specific antigens (hereinafter, referred to as "PSAs") which indicate that a subject has a prostate disease. That is, it is described that, as compared to blood samples originated from prostatic hyperplasia patients, those blood samples originated from prostate cancer patients contain a greater amount of a prostate-specific antigen having a specific sugar residue, i.e., an N-acetyl-D-galactosamine β1-4 N-acetylglucosamine (hereinafter, referred to as "LacdiNAc") residue (this prostate-specific antigen is hereinafter referred to as "LacdiNAc-PSA") and/or a fucose-α(1,2)-galactose β1,4 N-acetylglucosamine residue, in its sugar chain. This means that the onset of prostate cancer changes the sugar chains of PSAs and this leads to an increase in the amount of PSAs having the above-described specific sugar residue(s), as a result of which a high concentration of PSAs having the specific sugar residue (s) is observed in blood samples of prostate cancer patients. On the other hand, since the onset of prostatic hyperplasia does not cause such a change in the sugar chain, prostatic hyperplasia patients are not observed with a change in the concentration of PSAs having the specific sugar residue(s). On the basis of this, Patent Document 1 discloses a method of distinguishing prostate cancer by fraction measurement of sugar chains, which method is capable of distinguishing a prostate cancer patient from a prostatic hyperplasia patient by measuring, in their blood samples, the concentration of PSAs having the above-described specific sugar residue(s). In addition, for example, a method of identifying liver cancer by fraction measurement of α-fetoprotein (AFP) sugar chains and a method of identifying adenocarcinoma by fraction measurement of carcinoembryonic antigen (CEA) sugar chains have also been proposed.

Further, mucin-1 (hereinafter, referred to as "MUC1"), which is one of mucins that are high-molecular-weight glycoproteins, is also known as a tumor-associated antigen. MUC1 is widely expressed in the epithelial cells of normal glands, and it is known that the expression of MUC1 is drastically increased when the cells are malignant, for example, in breast cancer, ovarian cancer, lung cancer, pancreas cancer and bladder cancer; and that the glycosylation pattern changes in breast cancer and the like. Patent Documents 2 and 3 disclose an aptamer ligand and an anti-MUC1 antibody, both of which can be used for the quantification of such MUC1, respectively. Moreover, Patent Document 4 describes that MUC1 and the like can be used as biomarkers of prostate cancer and colorectal cancer.

For specific detection of a glycoprotein containing a specific sugar residue in its sugar chain, proteins called lectin that are capable of specifically recognizing and binding to such sugar residue are widely utilized. This is because it is very difficult to prepare an antibody whose epitope is a sugar chain, particularly an antibody whose epitope is a specific sugar residue, and such an antibody is thus hardly available. Lectins not only are inexpensive and available in a large amount but also have excellent protein stability and can thus be stored over a long time.

For example, *Wisteria floribunda* lectin (*Wisteria floribunda* agglutinin: hereinafter, referred to as "WFA") is known to have N-acetylgalactosamine as its primary binding sugar residue. Patent Document 1 discloses a method in which WFA having such a property is bound to a carrier and loaded to a column and a PSA having a LacdiNAc residue in a side chain of an asparagine-linked sugar chain is subsequently fractionated and quantified by ELISA or the like. In addition, Patent Document 5 discloses a method in which a solid-phase anti-PSA antibody and a fluorescently labeled WFA are allowed to forma sandwich complex with a PSA having a LacdiNAc residue in a side chain of its sugar chain and this PSA having the specific sugar residue is then quantified by SPFS (Surface Plasmon-field enhanced Fluorescence Spectroscopy).

PRIOR ART REFERENCES

Patent Documents

[Patent Document 1] WO 2010/090264
[Patent Document 2] JP 2009-535051 A
[Patent Document 3] WO 2011/135869
[Patent Document 4] JP 2013-526852 A
[Patent Document 5] JP 2013-076666 A

SUMMARY OF THE INVENTION

Problems to be Solved by the Invention

Prostate cancer occurs primarily in men of 60 years and older. In Western countries, prostate cancer is the second leading cause of cancer-related death in men after lung cancer, and early detection of prostate cancer is thus desired. As a method of diagnosing prostate cancer, conventionally, a method in which all PSAs contained in a blood sample or the like are quantified as a total PSA value and this value is used as an index for determination is widely employed. Further, there is a method in which PSAs contained in a blood sample or the like that do not bind to α1-antichymotrypsin are quantified as free PSAs and the ratio of the amount of the free PSAs with respect to the total PSA amount (free PSA/total PSA ratio) is used as an index for determination.

For example, (1) a method of determining a high probability of prostate cancer based on a total PSA value of 10 ng/mL or greater and (2) a method of determining a high probability of prostate cancer based on a total PSA value of 4 to 10 ng/mL (gray zone) and a free PSA/total PSA ratio of 25% or lower have been employed. For a patient determined with a high probability of prostate cancer, a prostate gland biopsy is performed to obtain a definitive diagnosis. However, in the above-described diagnostic methods, there are relatively many cases where a patient of a benign disease such as prostatic hyperplasia, not prostate cancer, is also determined with a high probability of prostate cancer. Since a prostate gland biopsy is also performed for such patients of a benign disease and undue burden is thus placed on the patients, a diagnostic method capable of easily and highly accurately distinguishing prostate cancer from a benign disease has been desired.

In this respect, as described above, Patent Documents 1 and 5 disclose methods of distinguishing prostate cancer from prostatic hyperplasia, in which a lectin having an affinity for N-acetylgalactosamine residue, such as WFA, is brought into contact with a sample possibly containing a PSA; a PSA having an affinity for the lectin, namely a PSA having an N-acetylgalactosamine residue in its sugar chain, is quantified; and then prostate cancer is distinguished from prostatic hyperplasia based on the absolute amount of the specific PSA, that is, the concentration of the specific PSA in the blood sample, or the ratio of the amount of the specific PSA with respect to the amount of total PSA or free PSA. As a result of performing these methods, a prostatic hyperplasia patient who is potentially determined to have prostate cancer based only on the amount of total PSA or free PSA is correctly diagnosed with prostatic hyperplasia, not prostate cancer.

Although diagnostic methods with an improved accuracy of discriminating between prostate cancer and a benign prostate disease have been proposed as described above, an analysis method by which novel diagnostic information that enables to further improve the discrimination accuracy is continuously desired.

An object of the present invention is to provide an analysis method by which novel diagnostic information that enables to accurately distinguish prostate cancer from a benign prostate disease can be obtained.

Technical Solution

The present inventors discovered that, as compared to a blood sample originated from a prostate cancer patient or healthy individual, a blood sample originated from a benign prostate disease patient contains a greater amount of MUC1. Based on this discovery, the present inventors also discovered that a benign prostate disease and prostate cancer can be distinguished and diagnosed with good accuracy by quantifying all of MUC1s in a blood sample that are reactive with an anti-MUC1 antibody, preferably an anti-KL-6 monoclonal antibody, and utilizing this information, thereby completing the present invention. That is, the present invention enables to prevent a benign prostate disease patient from being misdiagnosed with prostate cancer and receiving unnecessary medical interventions.

In one aspect, the present invention provides methods of analyzing diagnostic information according to the following [1] to [6].

[1] A method of analyzing diagnostic information, the method comprising: measuring the concentration of all mucin-1s (total MUC1) in a blood sample originated from a subject to be diagnosed; comparing the thus measured value with a threshold value; and estimating that a disease affecting the subject to be diagnosed is not prostate cancer but a benign prostate disease when the measured value of the concentration of total MUC1 is greater than the threshold value.

[2] A method of analyzing diagnostic information for estimating which of a benign prostate disease and prostate cancer is affecting a subject to be diagnosed, the method using a combination of: a method of analyzing diagnostic information that comprises: measuring the concentration of all mucin-1s (total MUC1) in a blood sample originated from the subject to be diagnosed; comparing the thus measured value with a threshold value; and estimating that the disease affecting the subject to be diagnosed is not prostate cancer but the benign prostate disease when the measured value of the concentration of total MUC1 is greater than the threshold value; and diagnostic information relating to a prostate-specific antigen which indicates that the subject to be diagnosed has a prostate disease.

[3] A method of analyzing diagnostic information for estimating which of a benign prostate disease and prostate cancer is affecting a subject to be diagnosed, the method using a combination of: a method of analyzing diagnostic information that comprises: measuring the concentration of all mucin-1s (total MUC1) in a blood sample originated from the subject to be diagnosed; comparing the thus measured value with a threshold value; and estimating that the disease affecting the subject to be diagnosed is not prostate cancer but the benign prostate disease when the measured value of the concentration of total MUC1 is greater than the threshold value; and a method of analyzing diagnostic information that comprises: measuring the concentration of a prostate-specific antigen (LacdiNAc-PSA) which is reactive with a lectin that recognizes and binds to an N-acetyl-D-galactosamine β1-4 N-acetylglucosamine residue in the blood sample originated from the subject to be diagnosed; comparing the thus measured value with a threshold value; and estimating that the disease affecting the subject to be diagnosed is not the benign prostate disease but prostate cancer when the measured value of the concentration of LacdiNAc-PSA is greater than the threshold value.

[4] A method of analyzing diagnostic information, which estimates that, in a case where a subjected to be diagnosed is estimated to have prostate cancer by the method of analyzing diagnostic information according [3], the prostate cancer affecting the subject to be diagnosed is highly metastatic prostate cancer, prostate cancer accompanied by a benign prostate disease or hormone-resistant prostate cancer when not only a measured value of total MUC1 concentration is greater than another threshold value that is larger than the threshold value according to [3] but also a measured value of LacdiNAc-PSA concentration is greater than another threshold value that is larger than the threshold value according to [3].

[5] The method of analyzing diagnostic information according to any one of [1] to [4], wherein the benign prostate disease is prostatic hyperplasia.

[6] The method of analyzing diagnostic information according to any one of [1] to [5], wherein the total MUC1 is reactive with an anti-KL-6 monoclonal antibody.

In another aspect, the present invention provides diagnostic kits according to the following [7] to [10].

[7] A diagnostic kit for performing the method of analyzing diagnostic information according to [1], the kit comprising an anti-mucin-1 antibody for quantifying total MUC1.

[8] A diagnostic kit for performing the method of analyzing diagnostic information according to [2], the kit comprising: an anti-mucin-1 antibody for quantifying total MUC1; and an anti-prostate-specific antigen antibody for quantifying an anti-prostate-specific antigen.

[9] A diagnostic kit for performing the method of analyzing diagnostic information according to [3] or [4], the kit comprising: an anti-mucin-1 antibody for quantifying total MUC1; and LacdiNAc-PSA antibody and a lectin that recognizes and binds to an N-acetyl-D-galactosamine β1-4 N-acetylglucosamine residue for quantifying LacdiNAc-PSA.

[10] The diagnostic kit according to any one of [7] to [9], wherein the anti-mucin-1 antibody is an anti-KL-6 monoclonal antibody.

[11] The diagnostic kit according to any one of [7] to [10], which further comprises an instruction manual that describes information required for performing the method of analyzing diagnostic information.

Advantageous Effects of Invention

The use of the diagnostic information obtained by the analysis method of the present invention, by itself, enables to determine a benign prostate disease with high accuracy; however, by using such diagnostic information in combination with conventional prostate cancer-related diagnostic information that leads to an incorrect estimation of a benign prostate disease patient as a prostate cancer patient, the possibility of such a misdiagnosis given by a conventional diagnostic method can be drastically reduced.

BRIEF DESCRIPTION OF DRAWINGS

FIG. 1 is a scatter diagram that shows the results of the quantification step (1) of Example: Quantification of Total MUC1(KL6). It is noted here that "PC" represents the samples collected from prostate cancer patients and "BPH" represents the samples collected from prostatic hyperplasia patients.

FIG. 2 is a scatter diagram that shows, in an integrated manner, the results of the quantification step (1) of Example: Quantification of Total MUC1(KL6) (abscissa) and the results of the quantification step (2): Quantification of Total PSA (ordinate). It is noted here that "PC" represents the samples collected from prostate cancer patients and "BPH" represents the samples collected from prostatic hyperplasia patients.

FIG. 3 is a scatter diagram that shows, in an integrated manner, the results of the quantification step (1) of Example: Quantification of Total MUC1(KL6) (abscissa) and the results of the quantification step (3): Quantification of LacdiNAc-PSA (ordinate). It is noted here that "PC" represents the samples collected from prostate cancer patients and "BPH" represents the samples collected from prostatic hyperplasia patients; and that the sample circled with dotted line represents a sample originated from a patient with metastasis of prostate cancer to other site.

MODE FOR CARRYING OUT THE INVENTION

In the present specification, N-acetyl-D-galactosamine β1-4 N-acetylglucosamine, mucin-1 and *Wisteria floribunda* lectin are abbreviated as "LacdiNAc", "MUC1" and "WFA", respectively.

Further, a PSA which is used in the present invention and reactive with a lectin that recognizes a LacdiNAc residue as represented by WFA is referred to as "LacdiNAc-PSA", and all of PSAs including LacdiNAc-PSA and other PSAs are referred to as "total PSA".

—Analysis Method—

The first embodiment of the method of analyzing diagnostic information according to the present invention is a method of analyzing diagnostic information which comprises: measuring the concentration of all of MUC1s, namely total MUC1, in a blood sample originated from a subject to be diagnosed; comparing the thus measured value with a threshold value; and estimating that a disease affecting the subject to be diagnosed is not prostate cancer but a benign prostate disease when the measured value of the concentration of total MUC1 is greater than the threshold value.

In order to more clearly determine which of a benign prostate disease and prostate cancer is affecting the subject to be diagnosed, the diagnostic information that is obtained by the first embodiment of the analysis method of the present invention based on the total MUC1 concentration in a blood sample can be utilized in combination with prostate cancer-related diagnostic information provided by a prior art that cannot clearly distinguish a benign prostate disease from prostate cancer.

All of prior arts have a possibility of incorrectly estimating a benign prostate disease as prostate cancer, and the prostate cancer-related diagnostic information provided by a prior art is not particularly restricted and can be obtained by any known method of analyzing diagnostic information. For example, diagnostic information based on the concentration of all of PSAs in a blood sample, which is conventionally and commonly used, or diagnostic information based on the concentration of a specific sugar residue-containing PSA in a blood sample, which is described in WO 2010/090264 (Patent Document 1) and JP 2013-76666 A (Patent Document 5), can be utilized.

Accordingly, the second embodiment of the method of analyzing diagnostic information according to the present invention can be, for example, a method of analyzing diagnostic information for estimating which of a benign prostate disease and prostate cancer is affecting a subject to be diagnosed, the method using a combination of: a method of analyzing diagnostic information obtained by the first embodiment; and a method of analyzing diagnostic information that comprises: measuring the concentration of all of PSAs, namely total PSA, in a blood sample originated from the subject to be diagnosed; comparing the thus measured value with a threshold value and; and estimating that the disease affecting the subject to be diagnosed is not the benign prostate disease but prostate cancer when the measured value of the concentration of total PSA is greater than the threshold value.

In the above-described second embodiment, as a method of analyzing diagnostic information that is used in combination with a method of analyzing diagnostic information obtained by the first embodiment, a method of using the value of total PSA was exemplified; however, as described above, a method of analyzing diagnostic information that uses the ratio of the amount of free PSAs with respect to the total PSA amount (free PSA/total PSA ratio) as well as other known method of analyzing diagnostic information may be used.

The third embodiment of the method of analyzing diagnostic information according to the present invention is a method of analyzing diagnostic information for estimating which of a benign prostate disease and prostate cancer is affecting a subject to be diagnosed, the method using a combination of: a method of analyzing diagnostic information obtained by the first embodiment; and a method of analyzing diagnostic information that comprises: measuring the concentration of a PSA which is reactive with a lectin that recognizes and binds to a LacdiNAc residue, namely LacdiNAc-PSA, in a blood sample originated from the subject to be diagnosed; comparing the thus measured value with a threshold value; and estimating that the disease affecting the subject to be diagnosed is not the benign prostate disease but prostate cancer when the measured value of the concentration of LacdiNAc-PSA is greater than the threshold value.

Further, the fourth embodiment of the method of analyzing diagnostic information according to the present invention is a method of analyzing diagnostic information which estimates that, in a case where a subjected to be diagnosed is estimated to have prostate cancer by the method of analyzing diagnostic information according to the third embodiment, the prostate cancer affecting the subject to be diagnosed is highly metastatic prostate cancer, prostate cancer accompanied by a benign prostate disease or hormone-resistant prostate cancer when not only a measured value of total MUC1 concentration is greater than another threshold value (second threshold value relating to total MUC1) that is larger than the threshold value according to the third embodiment (first threshold value relating to total MUC1) but also a measured value of LacdiNAc-PSA concentration is greater than another threshold value (second threshold value relating to LacdiNAc-PSA) that is larger than the threshold value according to the third embodiment (first threshold value relating to LacdiNAc-PSA).

In the present invention, it is preferred that "total MUC1" be reactive with an "anti-KL-6 monoclonal antibody". That is, in the measurement of the concentration of total MUC1, an anti-MUC1 antibody is usually used as an antibody for immobilization or labeling, and it is preferred to use an anti-KL-6 monoclonal antibody as the anti-MUC1 antibody.

There are several MUC1 variants; however, anti-MUC1 antibodies include monoclonal antibodies that recognize and bind to a moiety common to all of or the majority of the variants as an epitope, as well as monoclonal antibodies that bind to some of the variants, such as an anti-KL-6 monoclonal antibody that recognizes a sialylated sugar chain antigen KL-6 (an antigen composed of an amino acid sequence PDTRPAP and a sialylated sugar chain bound to the threonine (T) thereof, which is Neu5Acα2-3Galβ1-3GalNAcα sugar chain) as an epitope and an anti-CA15-3 monoclonal antibody. In the present invention, a variety of anti-MUC1 antibodies can be used for the analysis of diagnostic information and, as one of such embodiments, a highly reliable analysis can be performed using an anti-KL-6 monoclonal antibody. In the following descriptions of the present specification, as a preferred embodiment, the term "anti-MUC1 antibody" is interchangeable with the term "anti-KL-6 monoclonal antibody".

Specifically, in the above-described first to fourth embodiments, when an "anti-KL-6 monoclonal antibody" is used as an "anti-MUC1 antibody" for measuring the concentration of "total MUC1" in the mode of a sandwich assay such as SPFS or ELISA, the "total MUC1" for which the concentration is thus measured means all of MUC1s that are reactive with the anti-KL-6 monoclonal antibody (hereinafter, referred to as "total MUC1(KL6)").

The matters relating to the first to fourth embodiments will now be described sequentially.

Blood Sample

In the analysis method of the present invention, as a sample for the measurement of the concentration of a specific glycoprotein, a blood sample originated from a subject to be diagnosed is used.

The subject to be diagnosed is typically a human; however, it may also be a non-human mammal such as a human disease model animal (e.g., mouse, rat, guinea pig, rabbit, goat, cat, dog, pig or monkey).

An example of a preferred human subject to be diagnosed is a patient for whom it is necessary to improve the diagnostic accuracy and to clarify whether or not the patient has prostate cancer because, although other diagnostic method strongly indicates that the patient has prostate cancer, the possibility of the affecting disease being a benign prostate disease cannot be eliminated.

The benign prostate disease is typically prostatic hyperplasia (benign prostatic hyperplasia: BPH); however, examples thereof also include other prostate gland-related benign diseases, such as prostatitis.

The blood sample may be whole blood, or serum or plasma prepared from whole blood. Further, the blood sample may contain an anticoagulant that is added at the time of blood collection, as well as a diluent, a reagent and the like that are added as required after the collection. The blood sample can be collected and prepared in accordance with a known method.

Lectin

In the third and fourth embodiments of the analysis method of the present invention, a lectin that recognizes and binds to a LacdiNAc residue is used for the quantification of LacdiNAc-PSA. A representative example of such a lectin is WFA; however, lectins that can be used in the present invention are not restricted thereto. That is, any lectin can be used in the present invention in the same manner as WFA, as long as the lectin is capable of recognizing and binding to a LacdiNAc residue contained in a sugar chain of LacdiNAc-PSA and can be utilized for the measurement of the concentration of LacdiNAc-PSA in a blood sample.

Examples of the lectin used in the third embodiment of the analysis method of the present invention also include *Trichosanthes japonica* lectin-II (TJA-II) which recognizes and binds to both a β-GalNAc residue and a fucose-α(1,2)-galactose residue.

WFA also recognizes and binds to galactose in addition to a Tn residue and a LacdiNAc residue; however, such binding does not cause a problem in the execution of the present invention because the strength of the binding is extremely weak and the binding constant of galactose is lower than that of WFA by several orders.

As for a lectin other than WFA, it is preferred that the lectin be capable of recognizing and binding to only a Tn residue and a LacdiNAc residue among sugar residues; however, any lection can be used in the present invention as long as the ability of the lectin to recognize and bind to a sugar residue other than Tn residue and LacdiNAc residue is sufficiently weak in a range that causes substantially no problem in the execution of the present invention.

Quantification Method

When performing the analysis method of the present invention, it is necessary to measure and quantify an item(s) that is/are required for each embodiment and selected from three items of measurement targets, which are total MUC1, LacdiNAc-PSA and total PSA, or all of these three items of measurement targets. The method of quantifying these measurement targets is not particularly restricted as long as it is capable of yielding measured values with an accuracy sufficient for performing the analysis in each embodiment, and such a method can be appropriately selected from known quantification methods.

Examples of a preferred method of quantifying the measurement targets include SPFS (Surface Plasmon-field enhanced Fluorescence Spectroscopy) that is capable of quantifying a measurement target with high sensitivity and high accuracy. SPFS is a method which utilizes a phenomenon that, when an excitation light is irradiated to a metal thin film formed on a dielectric member at an angle that causes attenuated total reflection (ATR), an evanescent wave transmitting through the metal thin film is enhanced by several ten times to several hundred times due to resonance with surface plasmon, so as to efficiently excite a fluorescent substance labeling a measurement target captured in the vicinity of the metal thin film. By measuring the intensity of the fluorescence emitted from the fluorescent substance and comparing the thus measured value against the intensity of fluorescence measured using a standard sample having a known concentration, the concentration of the measurement target in a blood sample can be determined. Such SPFS is extremely sensitive as compared to common fluorescent labeling methods and the like; therefore, it is capable of determining the concentration of a measurement target even when the measurement target is contained in a sample at an extremely low concentration.

Among the three items which are the total MUC1 concentration, the LacdiNAc-PSA concentration and the total PSA concentration, for a plurality of measurement items that are required depending on each embodiment, the data required for final analysis may be obtained by repeatedly quantifying a single item or a plurality of items which do not meet the requirement for the final analysis by themselves; however, from the standpoints of an improvement in the efficiency of the measurement process, the reliability of the measurement results and the like, it is preferred to quantify a plurality of measurement items that are required depending on each embodiment altogether at once.

For example, by forming a plurality of assay areas corresponding to each measurement item on a single SPFS measuring member (hereinafter, referred to as "sensor chip"), a plurality of measurement items can be quantified simultaneously. Such an embodiment is preferred because, as compared to an embodiment where a plurality of sensor chips are used to quantify the respective measurement targets, not only the cost and time required for the quantification can be cut down by reduction in the required members and reagents as well as the number of steps, but also variations in the measured values that are attributed to the differences among sensor chips can be reduced by the use of a single sensor chip.

Further, in the present invention, diagnostic information is analyzed based on the concentrations of total MUC1, LacdiNAc-PSA and total PSA in a blood sample; however, it is also possible to, for the analysis, directly use "measured values" obtained by a quantification method such as SPFS in accordance with a prescribed measurement protocol, without converting each "measured value" into "concentration" expressed in a prescribed unit such as ng/mL. For example, in SPFS, a measured value of fluorescence intensity is usually expressed in an arbitrary unit (a.u.), and this measured value that reflects the concentration of a measurement target in a blood sample may be used to set a threshold value and perform the analysis of diagnostic information.

Embodiments Based on SPFS

The fundamental constitutions for performing SPFS, namely embodiments of a sensor chip, a measuring apparatus, a system, measurement procedure and the like, are known, and they can be applied to appropriately carry out the present invention. In SPFS, a measurement target is generally quantified in the mode of a sandwich assay where a ternary complex composed of an immobilization probe (antibody), the measurement target and a fluorescent-labeling probe (lectin or antibody) is formed.

Among the total MUC1, LacdiNAc-PSA and total PSA, for the quantification of LacdiNAc-PSA that is glycoproteins having a specific sugar residue, there are two representative quantification methods.

The first quantification method is a method in which, without fractionating glycoproteins using a lectin that recognizes and binds to a specific sugar residue, the entire blood sample (glycoproteins) is subjected to SPFS and, among those glycoproteins that are captured by an immobilization probe (antibody), ones having a specific sugar residue are quantified by fluorescently labeling them with a fluorescent-labeling probe (lectin) that binds to the specific sugar residue. Although glycoproteins that do not have the specific sugar residue also bind to the immobilization probe, since the fluorescent-labeling probe (lectin) recognizing the specific sugar residue does not bind thereto, such glycoproteins are not quantified. For example, JP 2013-76666 A (Patent Document 5) discloses a method of quantifying a specific glycoprotein (PSA) by SPFS using a specific lectin (e.g., WFA) in the same manner as in the above-described first quantification method, and reference can be made to this method.

The second quantification method is a method in which, after fractionating a glycoprotein having a specific sugar chain in advance using a lectin that recognizes and binds to the specific sugar residue, only the thus obtained fractions of the glycoprotein are subjected to SPFS and the glycoprotein having the specific sugar chain that is captured by an immobilization probe (antibody) is quantified by fluorescently labeling the glycoprotein with a fluorescent-labeling probe (lectin) that binds thereto. Both of these methods can quantify LacdiNAc-PSA, which shows reactivity with a lectin recognizing a specific sugar residue and with an anti-PSA antibody. For example, WO2010/090264 (Patent Document 1) discloses a method in which a fraction containing a specific glycoprotein (PSA) is purified using a column (lectin affinity column) loaded with a carrier bound with a specific lectin (e.g., WFA) and the thus purified glycoprotein is quantified by ELISA, and reference can be made to this method.

A fractionation method using a lectin affinity column is summarized as follows. First, in accordance with a conventional method, a lectin affinity column is prepared by allowing a carrier for the column to react with a lectin that recognizes and binds to a specific sugar residue corresponding to a measurement target. Next, in accordance with a conventional method, a blood sample is applied to the thus prepared lectin affinity column so as to allow the measurement target having the specific sugar residue in the blood sample to bind to the lectin. Fractions containing substances that do not bind to the lectin (unbound fractions) are recovered as effluent by adding a washing buffer to the column. Then, fractions containing the measurement target bound with the lectin (bound fractions) are recovered as eluent by adding an elution buffer to the column. In this elution buffer, a hapten sugar capable of dissociating the measurement target bound with the lectin is dissolved. The hapten sugar may be selected in accordance with the lectin and, for example, when WFA is used as the lectin, GalNAc can be used as the hapten sugar.

(1) Quantification of Total MUC1

Examples of a method of quantifying the total MUC1 include a method in which a ternary sandwich immunocomplex composed of an anti-MUC1 antibody immobilized on the surface of a sensor chip (immobilized anti-MUC1 antibody), MUC1 and an anti-MUC1 antibody bound with a fluorescent substance (fluorescently labeled anti-MUC1 antibody) is formed.

The anti-MUC1 antibody can be prepared by a known method, or it can be purchased as a commercially available product. From the standpoint of the measurement stability, a monoclonal antibody is more preferably used than a polyclonal antibody. Examples of a commercially available anti-MUC1 monoclonal antibody include VU-3D1, VU-12E1, VU-11E2, VU-12E1, VU-3C6, VU-13F11, VU-5F12, VU-4C2, VU-2G7, VU-4H5, VU-11D1, M4021209, M3A106, M9E7, Ma552, VU-3C6, SM3, DF3, No. 1, No. 3, M2C5, 3H2740, 175C5, 126E7, C595, 139H2, 9A102, 8L820, M2F1, M4H2, 1B7, M10G4, EPR1023, EP1024Y, X325, 115D8, 0C125 and X75. All of these anti-MUC1 monoclonal antibodies correspond to anti-KL-6 monoclonal antibodies.

The fluorescently labeled anti-MUC1 antibody can be prepared by binding a desired fluorescent substance to an anti-MUC1 antibody in accordance with a known method and, in this process, a commercially available fluorescent substance labeling kit or the like can also be used. The fluorescent substance is not particularly restricted and, for example, a known fluorescent dye that is capable of emitting an appropriate fluorescence in SPFS can be used.

In the quantification of total MUC1, the type of the anti-MUC1 antibody of the immobilized anti-MUC1 antibody may be the same as or different from that of the anti-MUC1 antibody of the fluorescently labeled anti-MUC1 antibody. Since MUC1s are extremely large molecules and contain a common repeating structure, they can be immobilized and fluorescently labeled with the same type of anti-MUC1 antibody.

(2) Quantification of LacdiNAc-PSA

Examples of the first method of quantifying LacdiNAc-PSA include a method in which the entire blood sample (PSA) is subjected to SPFS without fractionation of LacdiNAc-PSA and then a ternary sandwich immunocomplex composed of an anti-PSA antibody immobilized on the surface of a sensor chip (immobilized anti-PSA antibody), LacdiNAc-PSA and a phosphor-bound lectin for LacdiNAc-PSA (fluorescently labeled lectin for LacdiNAc-PSA) is formed.

The anti-PSA antibody can be prepared by a commonly used known method, or it can be purchased as a commercially available product. From the standpoint of the measurement stability, a monoclonal antibody is more preferably used than a polyclonal antibody. Examples of a commercially available anti-PSA monoclonal antibody include PS2, PS3, PS4, PS5, PS6, PS15, 2H9, 3B4, 5A6, 5G6, 8G4, 9A8, 9G2, PS1, 8A6, 2H9, 1H12 and No. 79. Further, in order not to prevent the fluorescently labeled lectin for LacdiNAc-PSA from recognizing and binding to a specific sugar residue in a sugar chain, it is preferred to use an antibody whose epitope is the protein moiety, not the sugar chain, of PSA.

The fluorescently labeled lectin for LacdiNAc-PSA can be prepared by binding a desired fluorescent substance to a lectin that recognizes a LacdiNAc residue as represented by WFA in accordance with a commonly used known method and, in this process, a commercially available fluorescent substance labeling kit or the like can also be used. The fluorescent substance is not particularly restricted and, for example, a known fluorescent dye that is capable of emitting an appropriate fluorescence in SPFS can be used.

However, depending on the embodiment of the present invention, for acquisition of prostate cancer-related diagnostic information, not only PSA having a LacdiNAc residue but also both of PSA having a LacdiNAc residue and PSA having a fucose-$\alpha$(1,2)-galactose residue can be the subject of quantification (see Patent Documents 1 and 5). In that case, the fluorescently labeled lectin for LacdiNAc-PSA can also be prepared using a lectin that recognizes both of the LacdiNAc residue and the fucose-$\alpha$(1,2)-galactose residue, such as *Trichosanthes japonica* lectin-II (TJA-II).

Examples of the second method of quantifying LacdiNAc-PSA include a method in which, after a LacdiNAc-PSA fraction is prepared from a blood sample using a lectin for LacdiNAc-PSA1 in advance, the LacdiNAc-PSA fraction is subjected to SPFS and then a ternary sandwich immunocomplex composed of an immobilized anti-PSA antibody, LacdiNAc-PSA and an anti-PSA antibody bound with a fluorescent substance (fluorescently labeled anti-PSA antibody) is formed.

The immobilized anti-PSA antibody used in this second method of quantifying LacdiNAc-PSA may be of the same type as the one used in the above-described first method of quantifying LacdiNAc-PSA.

The fluorescently labeled anti-PSA antibody can be prepared by binding a desired fluorescent substance to an anti-PSA antibody in accordance with a known method and, in this process, a commercially available fluorescent substance labeling kit or the like can also be used. The fluorescent substance is not particularly restricted and, for example, a known fluorescent dye that is capable of emitting an appropriate fluorescence in SPFS can be used.

(3) Quantification of Total PSA

Examples of a method of quantifying the total PSA include a method in which a ternary sandwich immunocomplex composed of an anti-PSA antibody immobilized on the surface of a sensor chip (immobilized anti-PSA antibody), PSA and an anti-PSA antibody bound with a phosphor (fluorescently labeled anti-PSA antibody) is formed.

The immobilized anti-PSA antibody used for the quantification of the total PSA may be of the same type as the one used for the quantification of LacdiNAc-PSA. Further, the fluorescently labeled anti-PSA antibody (fluorescent substance and/or anti-PSA antibody) used for the quantification of the total PSA may be of the same type as the fluorescently labeled anti-PSA antibody (fluorescent substance and/or anti-PSA antibody) used in the second method of quantifying LacdiNAc-PSA.

Embodiments Based on Other Quantification Method

Examples of a method used for the quantification of a measurement target other than SPFS include ELISA that is widely used as a method of quantifying a biologically relevant substance. In ELISA, a measurement target is generally quantified in the mode of a sandwich assay where a ternary complex composed of an immobilization probe (antibody), the measurement target and an enzyme-labeling probe (antibody or lectin) is formed, and the measurement target is quantified based on the amount of a dye (signal intensity) generated by reaction between the enzyme of the enzyme-labeling probe and a prescribed substrate.

In cases where LacdiNAc-PSA is quantified by ELISA, as in the above-described second method of quantifying LacdiNAc-PSA, it is required to separate in advance those fractions containing LacdiNAc-PSA from all of PSAs contained in a blood sample by utilizing a lectin that recognizes and binds to a specific sugar residue, for example, a lectin affinity column on which WFA is supported.

Basic methods for performing ELISA and fractionation are known, and the present invention can be appropriately carried out by applying these methods. For example, reference can be made to WO 2010/090264 (Patent Document 1) which describes, for example, a method of quantifying a specific glycoprotein, PSA, by utilizing ELISA and a lectin affinity column on which a specific lectin is supported.

Threshold Value

The threshold value that is used in the first embodiment as well as in the second, third and fourth embodiments utilizing the first embodiment for the purpose of determining whether or not a measured value of the total MUC1 concentration in a blood sample indicates the presence of a certain disease (first threshold value relating to the total MUC1) can be set by a commonly used method. For example, the total MUC1 concentration is measured for blood samples originated from a plurality of patients who have been definitively diagnosed with prostate cancer and blood samples originated from a plurality of patients who have been definitively diagnosed with a benign prostate disease such as prostatic hyperplasia, and the concentration at which the measured data of the latter are included at a certain reference ratio or higher is determined and defined as the threshold value for estimating that a subject has a benign prostate disease. This reference ratio of the measured data corresponds to the reliability relating to the estimation of a benign prostate disease, that is, the probability of correct estimation. A more reliable threshold value can be set by increasing the number of samples that represent the population of the measured data. When the total MUC1 concentration measured for a particular blood sample is compared against a threshold value set in this manner and the measured value of the total MUC1 concentration is greater than the threshold value, it can be estimated with a certain probability that this blood sample came from a subject to be diagnosed who has a benign prostate disease. It would be ideal if, from the measured data, a threshold value could be set such that a determination of 100% positive can be given when a blood sample originated from a subject to be diagnosed who has a benign prostate disease is analyzed and a determination of 100% negative can be given when a blood sample originated from a subject to be diagnosed who has prostate cancer is analyzed; however, it is realistically difficult to set such a threshold value. Taking into consideration the desired accuracy of the analysis, such a threshold value with which a positive determination can be obtained with a desirably high probability when a blood sample originated from a subject to be diagnosed who has a benign prostate disease is analyzed or, in other words, such a threshold value with which a probability of getting a false-positive determination can be minimized for the analysis of a blood sample originated from a subject to be diagnosed who has prostate cancer, can be set.

The threshold value used in the second embodiment against which the measured value of the total PSA concentration in a blood sample is compared and the threshold value used in the third embodiment against which the measured value of the LacdiNAc-PSA concentration in a blood sample is compared (first threshold value relating to LacdiNAc-PSA) can also be set in the same manner as described above.

Further, the threshold values against which the measured values of the total LacdiNAc-PSA concentration and the total PSA concentration in a blood sample are each compared (the second threshold values relating to LacdiNAc-PSA and total MUC1, respectively), which threshold values are used in the fourth embodiment for the detection of highly metastatic prostate cancer, prostate cancer accompanied by a benign prostate disease or hormone-resistant prostate cancer, can also be set in the same manner as described above. These threshold values used in the fourth embodiments are different from and usually larger than the threshold values used in the third embodiment for both LacdiNAc-PSA and total MUC1. The analysis in the third embodiment and the analysis in the fourth embodiment can be performed simultaneously because they are common in that the LacdiNAc-PSA concentration and the total MUC1 concentration in a blood sample are each compared against a prescribed threshold value.

—Kit—

In order to efficiently performing the method of analyzing diagnostic information according to the present invention, a kit can be configured by putting together necessary reagents and the like. The analysis of diagnostic information is typically performed using a quantification method based on a sandwich assay such as SPFS or ELISA and, as required, a fractionation method using a lectin affinity column in combination. Accordingly, the kit typically contains, as main constituents, reagents for the formation of a sandwich immunocomplex suitable for these methods, namely an antibody, which is a biologically relevant substance for immobilization, and a lectin or antibody, which is a biologically relevant substance for detection, and the kit may also contain, as required, a lectin for the preparation of a lectin affinity column as a constituent.

A kit for performing the first embodiment of the method of analyzing diagnostic information (first embodiment of the kit) can be configured to contain at least an anti-MUC1 antibody as a reagent for the quantification of total MUC1. This anti-MUC1 antibody is used for immobilization and binding on the surface of an SPFS sensor chip or ELISA substrate, as well as for the preparation of a fluorescently labeled anti-MUC1 antibody where the anti-MUC1 antibody is bound with a fluorescent substance when the quantification method is SPFS, or for the preparation of an enzyme-labeled anti-MUC1 antibody where the anti-MUC1 antibody is bound with an enzyme that reacts with a prescribed substrate and for detection when the quantification method is ELISA. Accordingly, in this case, the anti-MUC1 antibody comprises an anti-MUC1 antibody for immobilization and an anti-MUC1 antibody for detection; however, these anti-MUC1 antibodies may be of the same type.

A kit for performing the second embodiment of the method of analyzing diagnostic information (second embodiment of the kit) can be configured to contain at least the following reagents: an anti-MUC1 antibody as a reagent for the quantification of total MUC1; and an anti-PSA antibody as a reagent for the quantification of PSA.

With regard to the reagent for the quantification of total MUC1, the same descriptions as provided above for the first embodiment of the kit are applied.

For example, in the quantification of the total PSA, the anti-PSA antibody contained as a reagent for the quantification of PSA is used for immobilization and binding on the surface of an SPFS sensor chip or ELISA substrate, as well as for the preparation of a fluorescently labeled anti-PSA antibody where the anti-PSA antibody is bound with a fluorescent substance when the quantification method is SPFS, or for the preparation of an enzyme-labeled anti-PSA antibody where the anti-PSA antibody is bound with an enzyme that reacts with a prescribed substrate and for detection when the quantification method is ELISA. Accordingly, in this case, the anti-PSA antibody comprises an anti-PSA antibody for immobilization and an anti-PSA antibody for detection.

A kit for performing the third embodiment of the method of analyzing diagnostic information (third embodiment of the kit) can be configured to contain at least the following reagents: an anti-MUC1 antibody as a reagent for the quantification of total MUC1; and an anti-PSA antibody and a lectin that recognizes and binds to a LacdiNAc residue as reagents for the quantification of LacdiNAc-PSA.

With regard to the reagent for the quantification of total MUC1, the same descriptions as provided above for the first embodiment of the kit are applied.

In a case where LacdiNAc-PSA is quantified in accordance with the above-described first method, the anti-PSA antibody contained in the kit is used for immobilization and binding on the surface of an SPFS sensor chip or ELISA substrate. Meanwhile, the lectin that recognizes and binds to a LacdiNAc residue is bound with a fluorescent substance to prepare a fluorescently labeled lectin for LacdiNAc-PSA when the quantification method is SPFS, or it is bound with an enzyme that reacts with a prescribed substrate to prepare an enzyme-labeled lectin for LacdiNAc-PSA and used for detection when the quantification method is ELISA.

In a case where LacdiNAc-PSA is quantified in accordance with the above-described second method, the anti-PSA antibody contained in the kit is used for immobilization and binding on the surface of an SPFS sensor chip or ELISA substrate, as well as for the preparation of a fluorescently labeled anti-PSA antibody where the anti-PSA antibody is bound with a fluorescent substance when the quantification method is SPFS, or for the preparation of an enzyme-labeled anti-PSA antibody where the anti-PSA antibody is bound with an enzyme that reacts with a prescribed substrate and for detection when the quantification method is ELISA. Accordingly, in this case, the anti-PSA antibody comprises an anti-PSA antibody for immobilization and an anti-PSA antibody for detection. Meanwhile, the lectin that recognizes and binds to a LacdiNAc residue is used for the production of a lectin affinity column used for the preparation of LacdiNAc-PSA fractions.

As the anti-MUC1 antibody contained in the first to fourth embodiments of the kit, an anti-KL-6 monoclonal antibody is preferred. Particularly, in the embodiment where the kit contains both an anti-MUC1 antibody for immobilization and an anti-MUC1 antibody for detection, it is preferred that both of these anti-MUC1 antibodies be anti-KL-6 monoclonal antibodies.

The kits for performing the method of analyzing diagnostic information according to the respective embodiments may also contain, as required, a reagent other than the above-described ones, an instrument, an instruction manual and/or the like. Examples of such a reagent and instrument include: a reagent for immobilizing a prescribed antibody on the surface of an SPFS sensor chip or ELISA substrate; a reagent for binding a fluorescent substance to a prescribed lectin or antibody; a blocking liquid for inhibition of non-specific adsorption to the surface of an SPFS sensor chip or ELISA substrate; a washing liquid for liquid transfer after application of a blood sample and a reagent(s) in each step of SPFS; a reagent for binding a prescribed lectin to a carrier of a lectin affinity column; a reagent for washing a lectin affinity column or for preparing an elution buffer; a treatment liquid for a blood sample; an instrument for reaction of these reagents; a sensor chip for SPFS; a substrate for ELISA; and a carrier of a lectin affinity column. Further, in the instruction manual, information required for performing the method of analyzing diagnostic information according to each embodiment of the present invention, for example, methods (protocols) for using the above-described reagents and instruments and threshold values relating to the analysis of diagnostic information, can be described.

Examples

[Production/Preparation Steps]
(1) Production of Plasmon Excitation Sensor

After plasma-cleaning a 1 mm-thick glass transparent planar substrate ("S-LAL 10" manufactured by Ohara Inc., refractive index=1.72), a chromium thin film was formed on one side of this substrate by sputtering, and a gold thin film was further formed on the surface of this chromium thin film by sputtering. The chromium thin film had a thickness of 1 to 3 nm and the gold thin film had a thickness of 44 to 52 nm. The substrate on which a gold thin film was formed in this manner was immersed in an ethanol solution containing 10-carboxy-1-decanethiol (concentration=25 mg/mL) for at least 24 hours to form a SAM film on the surface of the gold thin film. The substrate was then removed from the ethanol solution and washed with ethanol and isopropanol, followed by drying using an air gun.

(2) Production of Flow Channel-Type Measuring Member for SPFS

On the surface of the plasmon excitation sensor (gold thin film) produced in the above-described step, a 0.5 mm-thick sheet-form silicone rubber spacer, which had a hole of 2 mm in width and 14 mm in length that served as a flow channel, was placed. A 2 mm-thick polymethyl methacrylate plate having a through-hole on both ends was further placed and press-adhered thereon, and the spacer and the plate were screw-fixed on the plasmon excitation sensor, thereby producing a flow channel-type measuring member for SPFS comprising a flow channel through which samples, reagents and the like could be transferred via the through-holes.

(3) Production of Fluorescently Labeled WFA

WFA (L-1350, manufactured by Vector Laboratories, Inc.) was fluorescently labeled using Alexa Fluor (trademark) 647 Protein Labeling Kit (manufactured by Invitrogen Corp.). The procedure of this process was in accordance with the protocol attached to the kit. In order to remove unreacted lectin and fluorescent dye, the reaction product was purified using an ultrafiltration membrane (manufactured by Nihon Millipore K.K.), and an Alexa Fluor 647-labeled WFA solution was thereby obtained. After determining the concentration of Alexa Fluor 647-labeled WFA in the thus obtained solution by measuring the absorbance, the solution was stored at 4° C.

(4) Production of Fluorescently Labeled Anti-MUC1 Antibody

An Alexa Fluor 647-labeled anti-MUC1 antibody was produced in the same manner as in the above step (3), except that a commercially available anti-MUC1 monoclonal antibody (anti-KL-6 monoclonal antibody) was used in place of WFA. It is noted here that, this anti-MUC1 monoclonal antibody was also used for the formation of an anti-MUC1 antibody-immobilized region as described below.

(5) Production of Fluorescently Labeled Anti-PSA Antibody

An Alexa Fluor 647-labeled anti-PSA antibody was produced in the same manner as in the above step (3), except that a commercially available anti-PSA monoclonal antibody (Clone No. 79, 2.5 mg/mL; manufactured by Mikuri Immunolaboratory, Ltd.) was used in place of WFA.

(6) Preparation of Blood Samples

Serum samples originated from patients who had been definitively diagnosed with prostate cancer and serum samples originated from patients who had been definitively diagnosed with prostatic hyperplasia were each 2- to 10-fold diluted with phosphate buffer to prepare blood samples.

[Quantification Steps]

For each of the blood samples prepared in the above production/preparation step (6), the concentration of each of total MUC1, LacdiNAc-PSA and total PSA was measured by the below-described procedures.

(1) Quantification of Total MUC1

(1-1) Formation of Anti-MUC1 Antibody-Immobilized Region

In the flow channel of the flow channel-type measuring member for SPFS that was produced in the above production/preparation step (2), using a peristaltic pump, ultrapure water and then phosphate-buffered physiological saline were circulated for 10 minutes and 20 minutes, respectively, at room temperature (25° C.) and a flow rate of 500 μL/min, thereby equilibrating the surface of the plasmon excitation sensor. Subsequently, 5 mL of a phosphate-buffered physiological saline containing 50 mM of N-hydroxysuccinimide and 100 mM of ethyl(dimethylaminopropyl)carbodiimide was circulated for 20 minutes. Thereafter, 2.5 mL of a commercially available anti-MUC1 monoclonal antibody (anti-KL-6 monoclonal antibody) solution was circulated for 30 minutes to immobilize the antibody on the SAM film, thereby forming an anti-MUC1 antibody-immobilized region. Further, a phosphate-buffered physiological saline containing 1% by weight of bovine serum albumin was circulated for 30 minutes to perform a non-specific adsorption-inhibiting treatment in the flow channel.

(1-2) Measurement by SPFS

Sample Application Step: In the flow channel in which the anti-MUC1 antibody-immobilized region was formed, the blood samples prepared in the above production/preparation step (6) were circulated for 25 minutes.

First Washing Step: A Tris-buffered physiological saline containing 0.05% by weight of Tween (registered trademark) 20 was circulated for 10 minutes.

Blank Measurement Step: With the flow channel being filled with the above-described Tris-buffered physiological saline, the metal thin film was irradiated with a laser light having a wavelength of 635 nm, whose photon amount was adjusted by an optical filter, from the back side of the plasmon excitation sensor through a prism. Then, using a CCD image sensor (manufactured by Texas Instruments Inc.) that was equipped with a ×20 objective lens and arranged above the assay area, the intensity of the light passing through a filter arranged for cutting wavelengths of non-fluorescent components was measured. Since the thus measured value is a noise value that does not include the fluorescence emitted by the phosphor labeling MUC1, the measured value is defined as "blank value".

Labeling Step: Then, 5 mL of a phosphate-buffered physiological saline containing the Alexa Fluor 647-labeled anti-MUC1 antibody produced in the above production/preparation step (4) (1 ng/mL) was circulated for 20 minutes.

Second Washing Step: A Tris-buffered physiological saline containing 0.05% by weight of Tween (registered trademark) 20 was circulated for 20 minutes.

Signal Measurement Step: With the flow channel being filled with the above-described Tris-buffered physiological saline, the light intensity was measured in the same manner as in the above-described blank measurement step. The thus measured value corresponds to a signal that includes the fluorescence emitted by the phosphor labeling MUC1.

(2) Quantification of Total PSA (2-1) Formation of Anti-PSA Antibody-Immobilized Region An anti-PSA antibody-immobilized region was formed in the same manner as in the above-described step (1-1) for the quantification of total MUC1, except that a commercially available anti-PSA monoclonal antibody was used in place of the anti-MUC1 monoclonal antibody.

(2-2) Measurement by SPFS

The total PSA was quantified in the same manner as in the above-described step (1-2) for the quantification of total MUC1, except that the Alexa Fluor 647-labeled anti-PSA antibody produced in the production/preparation step (5) was used in place of the Alexa Fluor 647-labeled anti-MUC1 antibody produced in the production/preparation step (4).

(3) Quantification of LacdiNAc-PSA (3-1) Formation of Anti-PSA Antibody-Immobilized Region An anti-PSA antibody-immobilized region was formed in the same manner as in the above-described step (1-1) for the quantification of total MUC1, except that a commercially available anti-PSA monoclonal antibody was used in place of the anti-MUC1 monoclonal antibody.

(3-2) Measurement by SPFS

LacdiNAc-PSA was quantified in the same manner as in the above-described step (1-2) for the quantification of total MUC1, except that the Alexa Fluor 647-labeled WFA produced in the production/preparation step (3) was used in place of the Alexa Fluor 647-labeled anti-MUC1 antibody produced in the production/preparation step (4).

[Analysis Steps]

FIG. 1 shows the results of the quantification step (1): Quantification of total MUC1(KL6). It is shown that the total MUC1(KL6) concentration was higher in the blood samples of prostatic hyperplasia patients than in those of prostate cancer patients. Therefore, it is seen that, based on these results, the concentration corresponding to a value in a range of, for example, 4.5 to 5 units can be set as the threshold value to be used in the first embodiment of the analysis method of the present invention.

FIG. 2 shows, in an integrated manner, the results of the quantification step (1): Quantification of total MUC1(KL6) (abscissa) and the results of the quantification step (2): Quantification of Total PSA (ordinate). It is shown that the total MUC1(KL6) concentration was higher in the blood samples of prostatic hyperplasia patients than in those of prostate cancer patients. That is, it is seen that, based on these results, the threshold value used in the analysis method of the present invention can be set in a range of, for example, 4.5 to 5 units. Therefore, it is understood that, in the second embodiment of the analysis method according to the present invention, even when the threshold value relating to the total PSA, which have been used in conventional diagnosis, includes a gray zone and this yields false-positive results in which a certain number of prostatic hyperplasia patients are diagnosed with prostate cancer, these false-positive patients can be correctly diagnosed with prostatic hyperplasia by using the total MUC1(KL6)-related threshold value in combination.

FIG. 3 shows, in an integrated manner, the results of the quantification step (1): Quantification of total MUC1(KL6) (abscissa) and the results of the quantification step (3): Quantification of LacdiNAc-PSA (ordinate). It is shown that the total MUC1(KL6) concentration was higher in the blood samples of prostatic hyperplasia patients than in those of prostate cancer patients. That is, it is seen that, based on these results, the threshold value used in the analysis method of the present invention can be set in a range of, for example, 4.5 to 5 units. Therefore, it is understood that, in the third embodiment of the analysis method according to the present invention, even when the threshold value relating to Lacdi-NAc-PSA, which is disclosed in Patent Document 1, includes a gray zone and this yields false-positive results in which a certain number of prostatic hyperplasia patients are diagnosed with prostate cancer, these false-positive patients can be correctly diagnosed with prostatic hyperplasia by using the total MUC1(KL6)-related threshold value in combination.

In FIG. 3, a sample having a high concentration of total MUC1(KL6) and a relatively high concentration of Lacdi-NAc-PSA is found (sample circled with dotted line), and this represents a sample originated from a patent with metastasis of prostate cancer to other site. Further, taking into consideration other results, it is believed that a similar result should also be obtained for a sample originated from a prostate cancer patient who also has a benign prostate disease such as prostatic hyperplasia. This is expected to be the same also for a sample originated from a hormone-resistant prostate cancer patient. Therefore, it is understood that, in the fourth embodiment of the present invention, highly metastatic prostate cancer, prostate cancer accompanied by a benign prostate disease or hormone-resistant prostate cancer can be detected by setting a second threshold value for both total MUC1(KL6) and LacdiNAc-PSA.

The invention claimed is:

1. A method for detecting a total mucin-1 in a subject, said method comprising:
   (a) measuring the concentration of said total mucin-1 in a blood sample originated from said subject, to provide a measured total mucin-1 concentration value;
   (b) determining a total mucin-1 threshold value comprising:
      (b)(1) measuring the concentration of said total mucin-1 in blood samples from a plurality of patients who have been diagnosed with prostate cancer,
      (b)(2) measuring the concentration of said total mucin-1 in blood samples from a plurality of patients who have been diagnosed with a benign prostate disease, and
      (b)(3) determining, as said total mucin-1 threshold value, the lowest concentration value measured from step (b)(2) which is higher than the majority of concentration values measured from step (b)(1); and
   (c) determining whether said measured total mucin-1 concentration value is greater than said total mucin-1 threshold value.

2. A method for detecting a total mucin-1 and a total prostate-specific antigen in a subject, said method comprising:
   (i) a first step comprising:
   (i)(a) measuring the concentration of said total mucin-1 in a blood sample originated from said subject, to provide a measured total mucin-1 concentration value;
   (i)(b) determining a total mucin-1 threshold value comprising:
      (i)(b)(1) measuring the concentration of said total mucin-1 in blood samples from a plurality of patients who have been diagnosed with prostate cancer,
      (i)(b)(2) measuring the concentration of said total mucin-1 in blood samples from a plurality of patients who have been diagnosed with a benign prostate disease, and
      (i)(b)(3) determining, as said total mucin-1 threshold value, the lowest concentration value measured from step (i)(b)(2) which is higher than the majority of concentration values measured from step (i)(b)(1); and
   (i)(c) determining whether said measured total mucin-1 concentration value is greater than said total mucin-1 threshold value; and
   measuring the concentration of said total prostate-specific antigen in said blood sample originated from said subject to provide a measured total prostate-specific antigen concentration value.

3. A method for detecting a total mucin-1 and a reactive prostate-specific antigen in a subject, said method comprising:
   (i) a first step comprising:
   (i)(a) measuring the concentration of said total mucin-1 in a blood sample originated from said subject, to provide a measured total mucin-1 concentration value;
   (i)(b) determining a total mucin-1 threshold value comprising:
      (i)(b)(1) measuring the concentration of said total mucin-1 in blood samples from a plurality of patients who have been diagnosed with a prostate cancer,
      (i)(b)(2) measuring the concentration of said total mucin-1 in blood samples from a plurality of patients who have been diagnosed with a benign prostate disease, and
      (i)(b)(3) determining, as said total mucin-1 threshold value, the lowest concentration value measured from step (b)(2) which is higher than the majority of concentration values measured from step (b)(1); and
   (i)(c) determining whether said measured total mucin-1 concentration value is greater than said total mucin-1 threshold value; and
   (ii) a second step comprising:
   (ii)(a) measuring the concentration of said reactive prostate-specific antigen, said reactive prostate-specific antigen being reactive with a lectin that recognizes and binds to an N-acetyl-D-galactosamine $\beta$1-4 N-acetyl-glucosamine residue, in said blood sample originated from said subject;
   (ii)(b) determining a reactive prostate-specific antigen threshold value comprising:
      (ii)(b)(1) measuring the concentration of said reactive prostate-specific antigen in blood samples from a plurality of patients who have been diagnosed with a prostate cancer,
      (ii)(b)(2) measuring the concentration of said reactive prostate-specific antigen in blood samples from a plurality of patients who have been diagnosed with a benign prostate disease, and
      (ii)(b)(3) determining, as said reactive prostate-specific antigen threshold value, the lowest concentration value measured from step (ii)(b)(2) which is higher than the majority of concentration values measured from step (ii)(b)(1); and
   (ii)(c) determining whether said measured total reactive prostate-specific antigen concentration value is greater than said reactive prostate-specific antigen threshold value.

4. The method according to claim 3, further comprising:
   (iii)(a) determining a second total mucin-1 threshold value which is greater than said total mucin-1 threshold value in step (i)(b) of claim 3, said determining comprising:

(iii)(a)(1) measuring the concentration of said total mucin-1 in blood samples from a plurality of patients who have been diagnosed as not having a condition selected from the group consisting of: highly metastatic prostate cancer, prostate cancer accompanied by a benign prostate disease, and hormone-resistant prostate cancer, (iii)(a)(2) measuring the concentration of said total mucin-1 in blood samples from a plurality of patients who have been diagnosed with said condition selected from the group consisting of: highly metastatic prostate cancer, prostate cancer accompanied by a benign prostate disease, and hormone-resistant prostate cancer, and (iii)(a)(3) determining, as said second total mucin-1 threshold value, the lowest concentration value measured from step (iii)(a)(2) which is higher than the majority of concentration values measured from step (iii)(a)(1);

(iii)(b) determining whether said measured total mucin-1 concentration value is greater than said second total mucin-1 threshold value;

(iii)(c) determining a second reactive prostate-specific antigen threshold value which is greater than said reactive prostate-specific antigen threshold value in step (ii)(b) of claim 3, said determining comprising:

(iii)(c)(1) measuring the concentration of said reactive prostate-specific antigen in blood samples from a plurality of patients who have been diagnosed as not having said condition selected from the group consisting of: highly metastatic prostate cancer, prostate cancer accompanied by a benign prostate disease, and hormone-resistant prostate cancer, (iii)(c)(2) measuring the concentration of said reactive prostate-specific antigen in blood samples from a plurality of patients who have been diagnosed with said condition selected from the group consisting of: highly metastatic prostate cancer, prostate cancer accompanied by a benign prostate disease, and hormone-resistant prostate cancer, and (iii)(c)(3) determining, as said second reactive prostate-specific antigen threshold value, the lowest concentration value measured from step (iii)(c)(2) which is higher than the majority of concentration values measured from step (iii)(c)(1); and (iii)(d) determining whether said measured reactive prostate-specific antigen concentration value is greater than said second reactive prostate-specific antigen threshold value.

5. The method according to claim 1, wherein said benign prostate disease is prostatic hyperplasia.

6. The method according to claim 1, wherein said total mucin-1 is reactive with an anti-KL-6 monoclonal antibody.

7. The method according to claim 2, wherein said benign prostate disease is prostatic hyperplasia.

8. The method according to claim 3, wherein said benign prostate disease is prostatic hyperplasia.

9. The method according to claim 2, wherein said total mucin-1 is reactive with an anti-KL-6 monoclonal antibody.

10. The method according to claim 3, wherein said total mucin-1 is reactive with an anti-KL-6 monoclonal antibody.

11. The method according to claim 5, wherein said total mucin-1 is reactive with an anti-KL-6 monoclonal antibody.

12. The method according to claim 7, wherein said total mucin-1 is reactive with an anti-KL-6 monoclonal antibody.

13. The method according to claim 8, wherein said total mucin-1 is reactive with an anti-KL-6 monoclonal antibody.

\* \* \* \* \*